United States Patent [19]
Tabata et al.

[11] Patent Number: 5,828,457
[45] Date of Patent: Oct. 27, 1998

[54] SAMPLE INSPECTION APPARATUS AND SAMPLE INSPECTION METHOD

[75] Inventors: Mitsuo Tabata, Yokohama; Toru Tojo, Naka-gun; Hisakazu Yoshino, Tokyo, all of Japan

[73] Assignees: Kabushiki Kaisha Toshiba, Kawasaki, Japan; Kabushiki Kaisha Topcon, Tokyo, Japan

[21] Appl. No.: 854,750

[22] Filed: May 12, 1997

Related U.S. Application Data

[63] Continuation of Ser. No. 413,174, Mar. 29, 1995, abandoned.

[30] Foreign Application Priority Data

Mar. 31, 1994 [JP] Japan .................................. 6-063744

[51] Int. Cl.$^6$ ............................. G01B 11/00; H01L 21/00
[52] U.S. Cl. ............................................ 356/394; 356/237
[58] Field of Search ................................... 356/394, 237; 382/144

[56] References Cited

U.S. PATENT DOCUMENTS 4,952,058  8/1990  Noguchi et al. ....................... 356/394
5,379,348  1/1995  Watanabe et al. .
5,404,410  4/1995  Tojo et al. .

FOREIGN PATENT DOCUMENTS 62-43129   2/1987  Japan .
4-100045   4/1992  Japan .

*Primary Examiner*—F. L. Evans
*Attorney, Agent, or Firm*—Oblon, Spivak, McClelland, Maier & Neustadt, P.C.

[57] ABSTRACT

A sample detection apparatus includes a light radiation unit, having an illumination lens and an objective lens, for radiating light on a sample on which a pattern relating to fabrication of a semiconductor device is formed. A light receiving unit detects a light transmission image of the pattern on the sample on which the light has been radiated by the light radiation unit. A determination unit determines a presence/absence of a defect of the pattern obtained by the light receiving unit with reference data relating to the pattern, and a control unit controls a ratio $\sigma$ of a numerical aperture of the objective lens, in accordance with a type of the pattern.

28 Claims, 11 Drawing Sheets

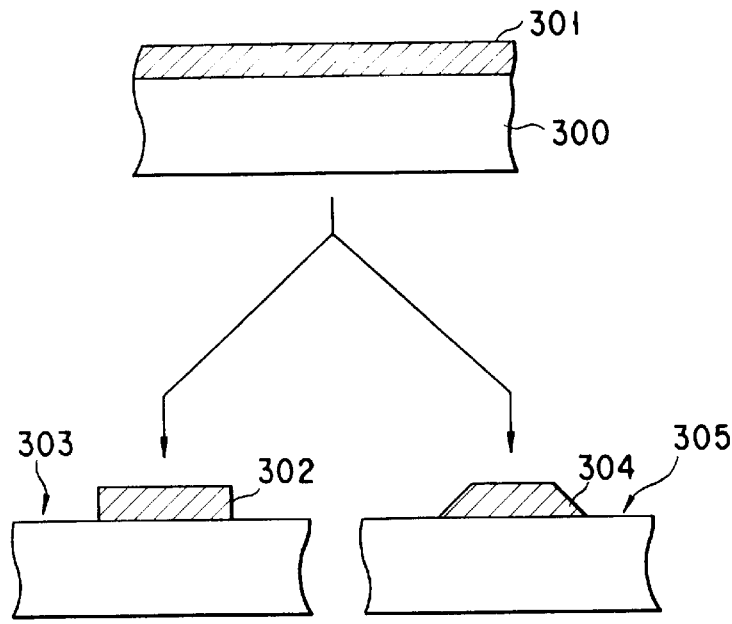
F I G. 5
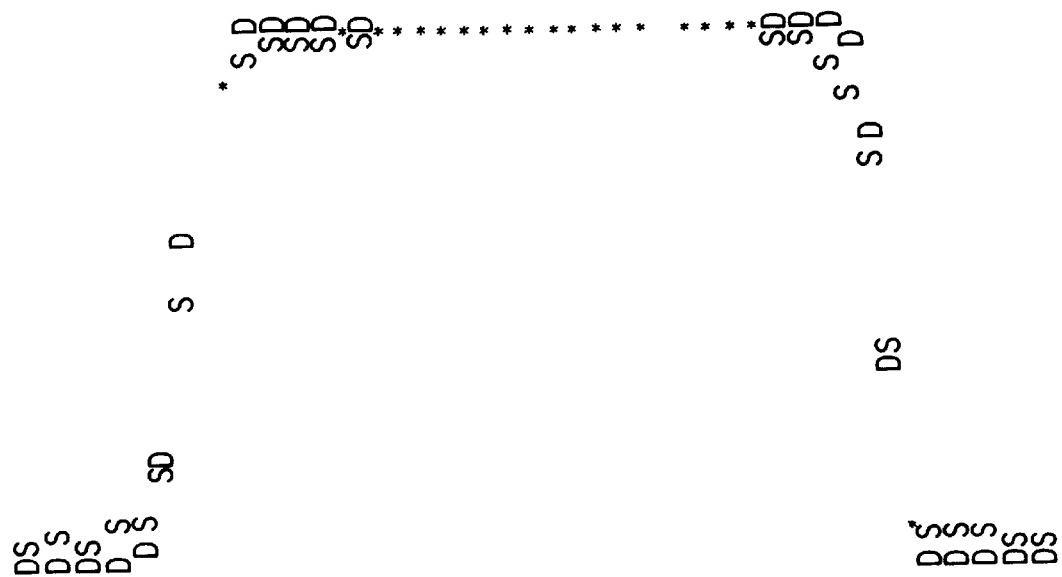
F I G. 6

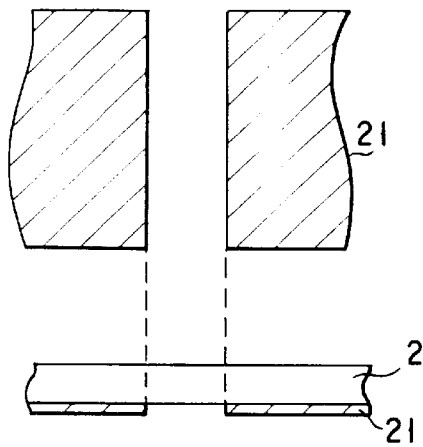
F I G. 7
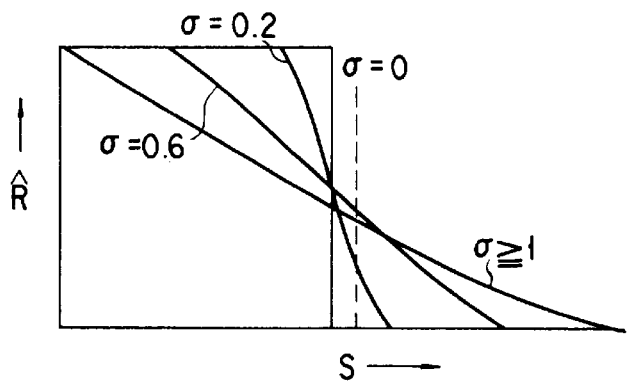
F I G. 8
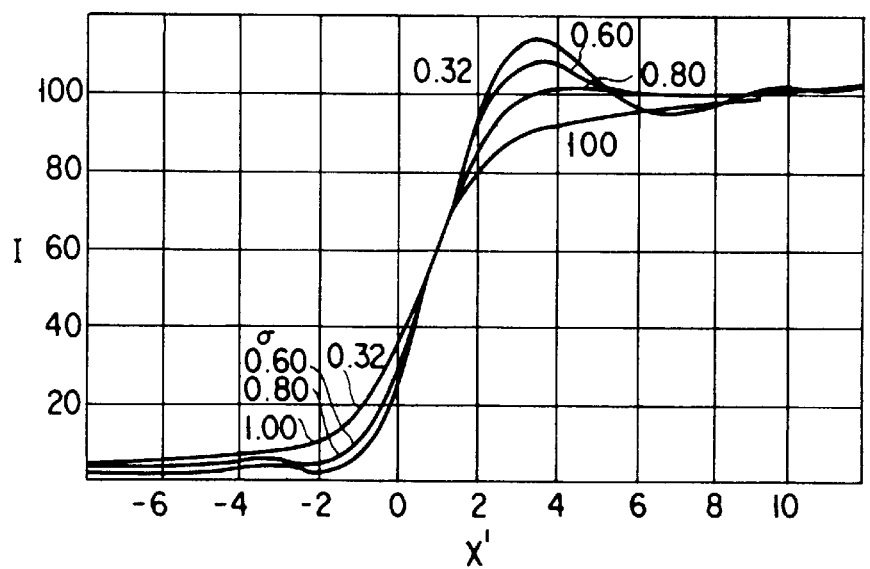
F I G. 9

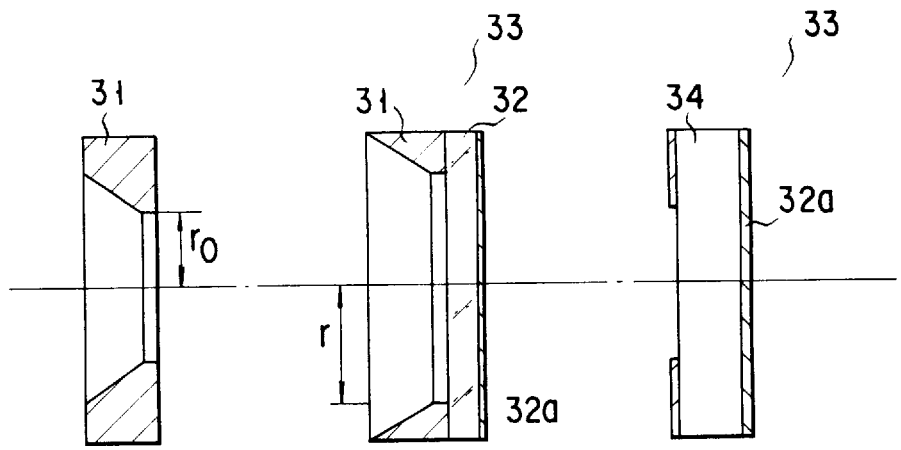
F I G. 12A   F I G. 12B   F I G. 12C
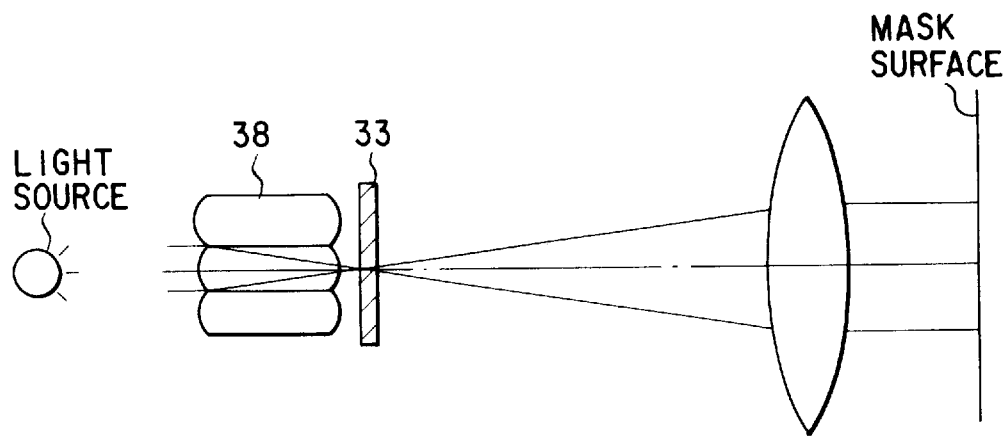
F I G. 14

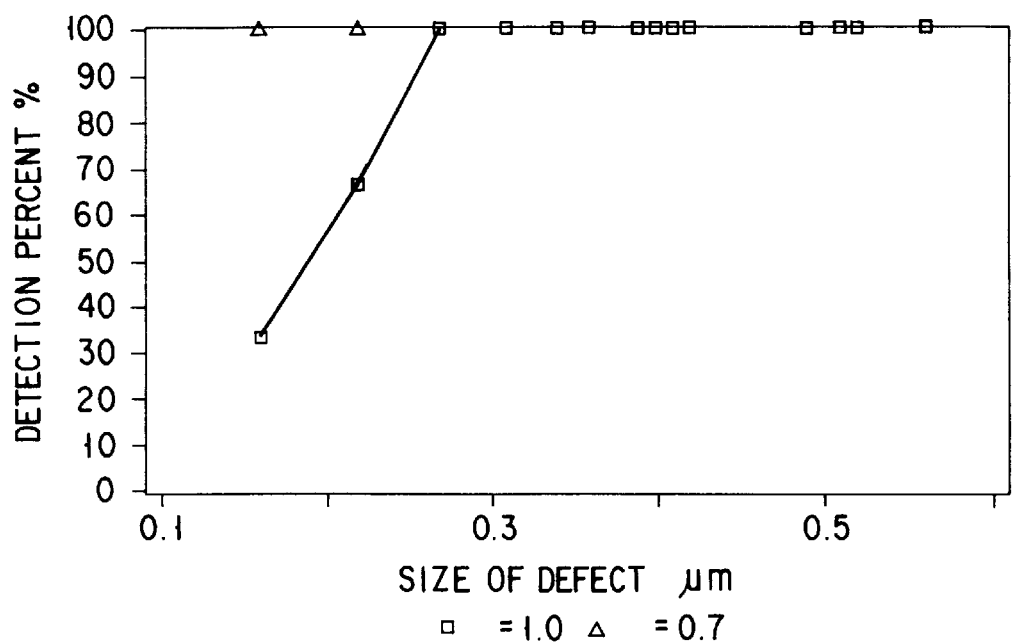
F I G. 17
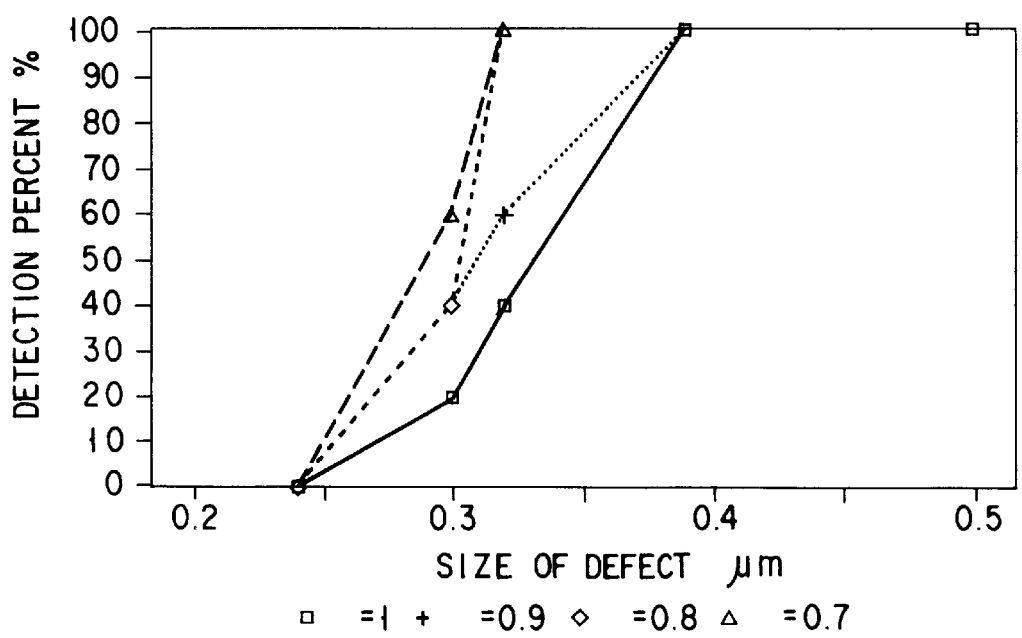
F I G. 18 ively determine the ratio of the numerical aperture of the illuminating lens to that of the objective lens. The reason for this
SAMPLE INSPECTION APPARATUS AND SAMPLE INSPECTION METHOD This application is a Continuation of application Ser. No. 08/413,174, filed on Mar. 29, 1995, now abandoned.

BACKGROUND OF THE INVENTION

1. Field of the Invention

The present invention relates to a sample inspection apparatus and a sample inspection method for inspecting samples such as a photo-mask, a wafer, a reticle and a liquid crystal substrate, on which patterns relating to the manufacturing of semiconductor devices are formed.

2. Description of the Related Art

A main cause of a decrease in the yield of large scale integration (LSI) circuits is a defect in a photo-mask used in fabricating a semiconductor device by means of lithography. With recent development of LSI, patterns formed on photo-masks have become thinner and accordingly it is necessary to detect a very small defect. Under the circumstances, sample inspection apparatuses for inspecting such small defects, such as defect inspection apparatuses and pattern inspection apparatuses, have been widely developed and put in practical use.

Conventional defect inspection apparatuses have been generally classified into two types. In one type, two chips with the same pattern are observed individually by different detection means, and both chips are compared by proper defect detection means to find a difference therebetween. In the other type, a chip with a pattern is observed by detection means, and the pattern is compared with pattern design data by defect detection means to detect a defect.

In the case of the former, since the two chips with the same pattern are observed individually, the same defect, if being present, cannot be detected. However, since it is not necessary to provide a circuit for processing the design data, the structure can be simplified. On the other hand, in the case of the latter, since an inspection is made on the basis of the design data, the detection of a defect is perfect but the structure is more complex.

In the above types of defect inspection apparatuses, in order to detect a very small defect, the resolution of the optical system needs to be enhanced, the comparative algorithm needs to be improved and the measuring signal processing method needs to be improved.

However, the detection sensitivity of defects is not yet satisfactory, and there is a demand for a sample inspection apparatus capable of detecting smaller defects. In particular, a sample inspection apparatus capable of detecting, with high sensitivity, a defect near an edge of a pattern has been desired.

It is generally known that in an optical microscope or a transfer apparatus, the resolution characteristics of the pattern can be enhanced by varying the ratio of the numerical aperture of an illuminating lens of an illuminating optical system to the numerical aperture of an objective lens, that is, by producing a partially coherent focused image. Since the above-mentioned inspection apparatus is basically constructed by the same optical system, the same advantage can be obtained by this method.

However, the number of types of patterns (e.g. a Cr pattern, a phase-shift pattern) to be inspected by the sample inspection apparatus is great, and it is difficult to definitively determine the ratio of the numerical aperture of the illuminating lens to that of the objective lens. The reason for this is that in the case of an inspection apparatus based on a design data base, the signal profile of an edge portion of a pattern varies, depending on the type of the pattern to be inspected (e.g. a Cr pattern, a phase-shift pattern) and the comparison algorithm must be changed, depending upon cases.

On the other hand, if the ratio of the numerical aperture of the illuminating lens to that of the objective lens is varied in accordance with the pattern to be inspected, a large variation occurs in radiation light amount and the gain of a light-receiving sensor varies greatly. As a result, a load on the circuit increases. In particular, since the gain width of the light-receiving sensor is increased to compensate a degradation of a light source, an additional increase in gain width is difficult.

SUMMARY OF THE INVENTION

It is an object of the invention to provide a sample inspection apparatus and a sample inspection method capable of detecting a defect of less dimensions than those of a defect which can be detected by a conventional apparatus, and, in particular, capable of detecting a defect near an edge of a pattern with high sensitivity.

The above object can be achieved by a sample inspection apparatus comprising:

a light source for radiating light on a sample on which a pattern relating to fabrication of a semiconductor device is formed;

an illumination lens provided between the light source and the sample, for illuminating light in the sample;

light receiving means for detecting a light transmission image of the pattern on the sample on which the light has been radiated by the light source;

an objective lens provided between the sample and the light receiving means for focusing an image of a pattern on the sample onto the light receiving means;

determination means for determining the presence/absence of a defect of the pattern by comparing measurement data corresponding to the light transmission image of the pattern obtained by the light receiving means with reference data relating to the pattern; and control means for controlling the ratio ($\sigma$) of the numerical aperture of the illumination lens to the numerical aperture of the objective lens, in accordance with the type of the pattern.

The above object can also be achieved by a sample detection apparatus comprising:

a light source for radiating light on a sample on which a pattern relating to fabrication of a semiconductor device is formed;

an illumination lens provided between the light source and the sample, for illuminating light in the sample;

light receiving means for detecting a light transmission image of the pattern on the sample on which the light has been radiated by the light source;

an objective lens provided between the sample and the light receiving means for focusing an image of a pattern on the sample onto the light receiving means;

determination means for determining the presence/absence of a defect of the pattern by comparing measurement data corresponding to the light transmission image of the pattern obtained by the light receiving means with reference data relating to the pattern; and control means for controlling the light radiation means such that the ratio ($\sigma$) of the numerical aperture of the illumination lens to the numerical aperture of the objective lens is varied and an output of the light receiving means is substantially constant when the ratio σ of the numerical aperture is varied.

The above object can also be achieved by a sample inspection method comprising the steps of:

radiating light on a sample, on which a pattern relating to fabrication of a semiconductor device is formed;

illuminating light on the sample;

receiving the light for detecting a light transmission image of the pattern on the sample on which the light has been radiated in the light radiation step;

focusing an image of a pattern on the sample;

determining the presence/absence of a defect of the pattern by comparing measurement data corresponding to the light transmission image of the pattern obtained in the light receiving step with reference data relating to the pattern; and controlling the ratio (σ) of the numerical aperture of the illumination lens to the numerical aperture of the objective lens, in accordance with the type of the pattern.

The above object can also be achieved by a sample inspection method comprising the steps of:

radiating light on a sample, on which a pattern relating to fabrication of a semiconductor device is formed;

illuminating light on the sample;

receiving the light for detecting a light transmission image of the pattern on the sample on which the light has been radiated in the light radiation step;

focusing an image of a pattern on the sample;

determining the presence/absence of a defect of the pattern by comparing measurement data corresponding to the light transmission image of the pattern obtained in the light receiving step with reference data relating to the pattern; and controlling the light radiation step, thereby executing an operation of varying the ratio (σ) of the numerical aperture of the illumination lens to the numerical aperture of the objective lens, and an operation of making an output in the light receiving step substantially constant even when the ratio σ of the numerical aperture is varied.

The above object can also be achieved by a sample inspection method wherein light is radiated on a sample on which a pattern relating to fabrication of a semiconductor device is formed, via an optical system having an illumination lens and an objective lens both having specified numerical apertures, thereby detecting a light transmission image of the pattern by light illuminating means, and the presence/absence of a defect of the pattern is determined by comparing measurement data corresponding to the light transmission image of the pattern obtained by the light receiving means with reference data relating to the pattern, the method comprising the steps of:

detecting a signal wave dull in the measurement data at an edge portion of the pattern; and compensating the wave dull detected in the detecting step by controlling the ratio (σ) of the numerical aperture of the illumination lens to the numerical aperture of the objective lens.

In the present invention, the ratio (σ) of the numerical aperture of the illumination lens to the numerical aperture of the objective lens is varied in accordance with the type of the pattern to be inspected and the variation in amount of light received by the light receiving element due to the variation of the ratio (σ) of the numerical aperture is reduced. Thereby, the defect detection sensitivity is enhanced and the load on the reception light sensor circuit can be reduced.

In addition, in the present invention, the ratio σ of the numerical aperture of the illumination lens to the numerical aperture of the objective lens is varied on the illumination lens side in accordance with the type of the pattern to be inspected. Thus, in the case of, e.g., a Cr pattern, the optimal ratio σ of the numerical aperture is $1 < \sigma \leq 0.65$. However, in the case of a half-tone phase shift pattern, the optimal ratio σ of the numerical aperture is 1, as in the prior art, with no overshoot of a measurement signal at a pattern edge. The ratio σ of the numerical aperture can be automatically altered to a desired value by the instruction of the operator. Furthermore, the load on the reception light sensor circuit can be reduced by virtue of, e.g., the filter means for controlling light transmissivity, which is provided on the aperture for varying the ratio σ of the numerical aperture, so that the amount of light received by the light receiving element may be set at a substantially constant value even when the ratio σ of the numerical aperture is varied.

As has been stated above, the conventional comparison algorithm is used and there are provided means for varying the ratio σ of the numerical aperture and means for controlling the amount of received light. Thus, a highly practical sample inspection apparatus can be provided, which meets various inspection conditions and has a reduced load on the reception light sensor circuit.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention in which.

FIG. 5 shows types of patterns;

FIG. 6 shows a difference between a measurement signal of a pattern and measurement data calculated from design data;

FIG. 7 shows a mask pattern from which the measurement signal shown in FIG. 6 is obtained;

FIG. 8 is a graph showing an optical response curve at the time value σ is varied;

FIG. 9 shows a measurement signal obtained at a pattern edge portion at the time value σ is varied;

FIGS. 12A, 12B and 12C show locations of an illumination optical system, where a σ stop mechanism according to the embodiment of the present invention is to be inserted;

FIG. 14 shows an example of an aperture fixing jig for inserting the σ stop mechanism of the present embodiment into the illumination optical system;

FIG. 17 is a characteristic graph showing the relationship between the dimensions of defects and the detection ratio in the case where edge defects were inspected according to the present invention; and FIG. 18 is a characteristic graph showing the relationship between the dimensions of defects and the detection ratio in the case where isolated defects were inspected according to the present invention.

DETAILED DESCRIPTION OF THE PREFERRED EMBODIMENTS

An embodiment of the present invention will now be described with reference to the accompanying drawings.

A mask defect inspection apparatus for inspecting a defect in a mask pattern by using design data will now be described as an example of a sample inspection apparatus according to the present invention.

Figure 1:
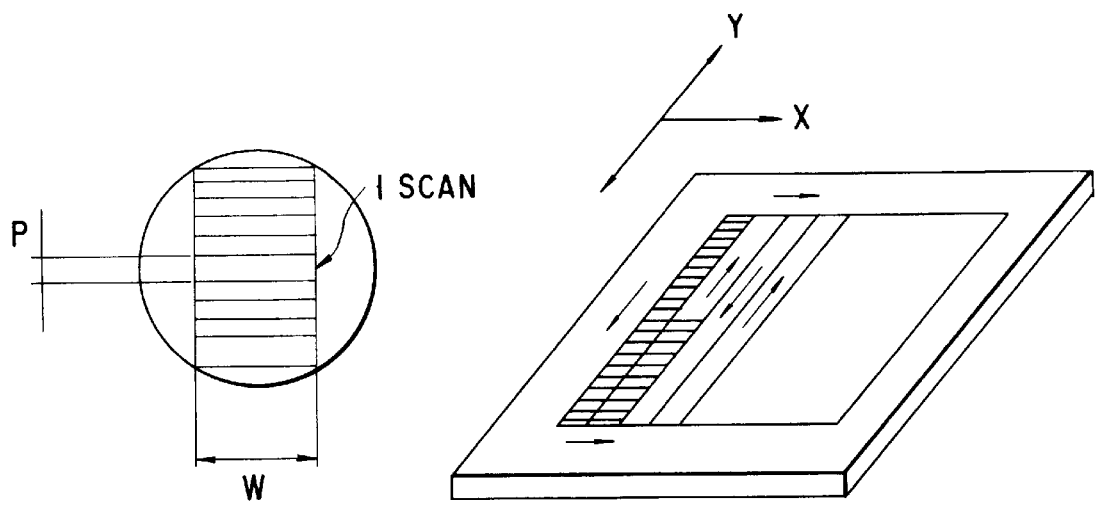
FIG. 1 illustrates an example of a scanning procedure of a sample inspection.
Figure 4:
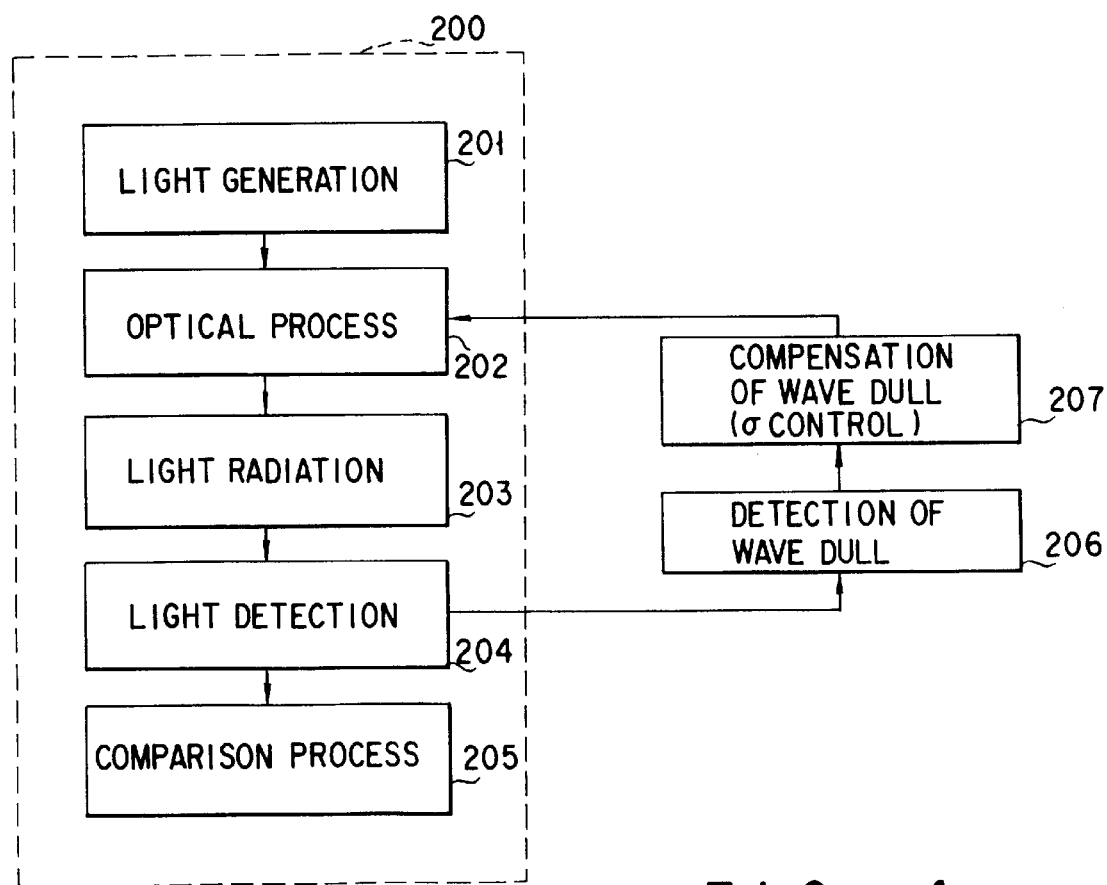
FIG. 4 is a flow chart illustrating the principle of the method of the present invention.

The principle of such a mask inspection is described, for example, in High-Precision Total Automated Inspection Apparatus for VLSIs, Electronic Material, p. 47 (September 1983). Specifically, the pattern defect inspection is carried out by enlarging a mask pattern with use of an optical system, etc. and successively measuring a thin strip portion (of the mask pattern) with a width of about 500 μm (actually a table is successively moved), as shown in FIG. 1. More specifically, while the table is being successively moved in a Y-direction, the strip portion is electrically scanned in succession in units of width P in an X-direction to obtain measurement signals. If one strip portion has completely been measured, the table is moved stepwise by width W in the X-direction, and while the table is successively moved once again in the Y-direction, the next strip portion is electrically scanned by the line sensor.

The mask defect inspection apparatus will now be described with reference to FIG. 2. A mask 2 is placed on an XYθ table 1. The mask 2 is illuminated by a proper light source 3 through an aperture 31 and an illumination lens 4. A pattern image obtained through the mask 2 is focused on a photodiode array (line sensor) 6 through an objective lens 5. A sense signal from the photodiode array 6 is A/D converted to measurement data by a sensor circuit 7. The measurement data along with position data from a position circuit 8 is delivered to a data comparison circuit 9.

On the other hand, design data of a pattern is sent from the magnetic disk apparatus 11 to a bit development circuit via a control computer 10, and figure data is digitized and sent to the data comparison circuit 9. In the data comparison circuit 9, the digitized bit pattern data is subjected to a proper filtering process and converted to multi-value data. Since the measurement data has been filtered due to the resolution characteristics of the objective lens 5 and the aperture effect of the photodiode array 6, the design data needs to be filtered to match with the measurement data. The measurement data and design data are compared according to a proper algorithm, and a non-coincidence portion of the design data and measurement data is determined to be a defect. The result of determination is sent to a display, etc. via an output circuit (not shown).

Figure 3:
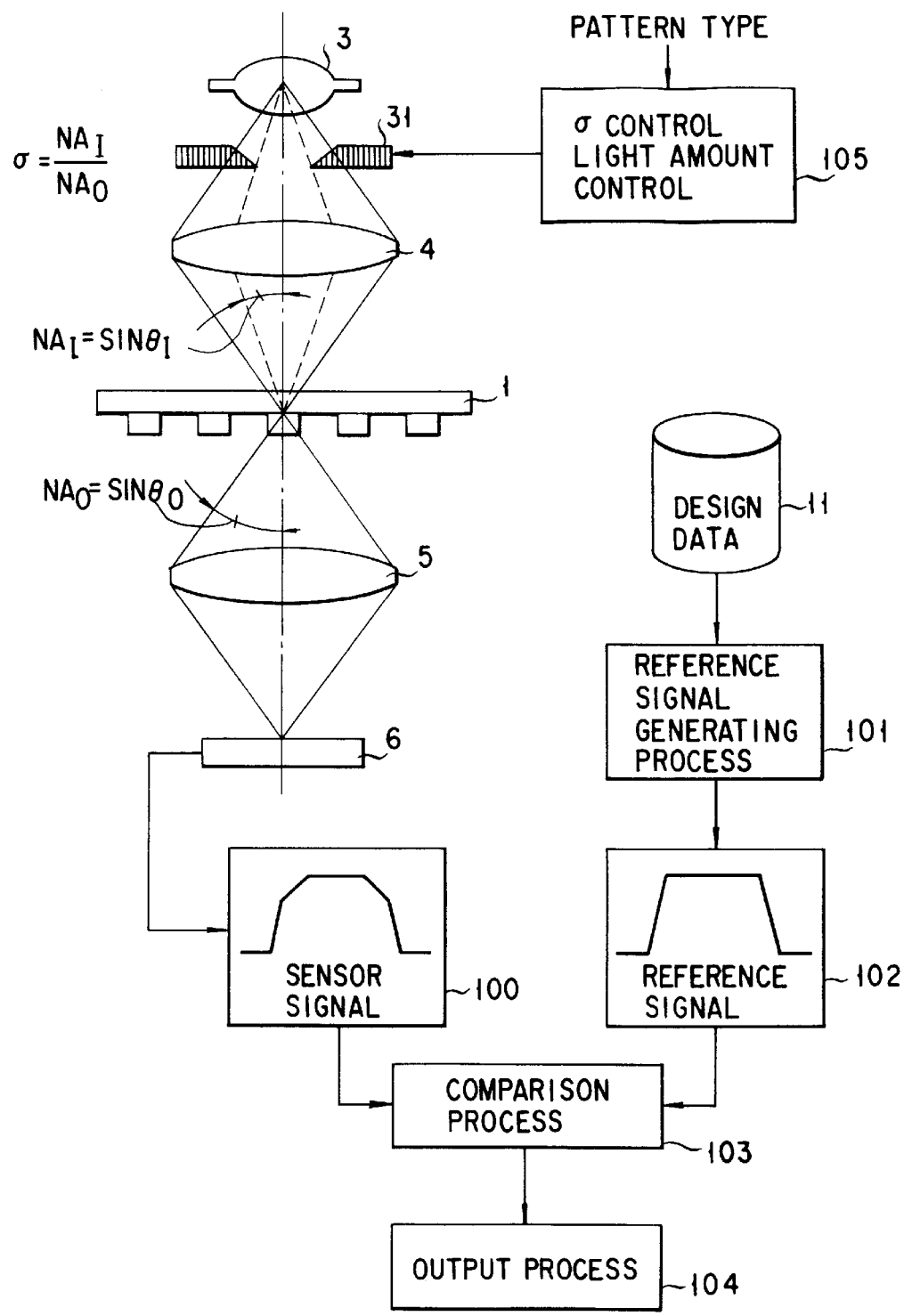
FIG. 3 shows in detail a main part of the apparatus as shown in FIG. 2.

FIG. 3 shows a main part of the present mask defect inspection apparatus. Measurement data 100 of a pattern image obtained through the mask and photodiode array 6 and a reference signal 102 read out from the magnetic tape apparatus 11 and generated through a reference signal generating process 101 are subjected to a comparison process 103, and a comparison result is output (104). The aperture 31 is subjected to a ratio σ control and a light amount control (105). The reference signal 102 is design data of a pattern of the mask 1 to be inspected or measurement data of a pattern other than the pattern to be inspected.

With the above hardware construction, mask defect inspection 200 of the present invention comprises: light generation 201 by the light source; optical process 202 for light produced by the functions of the illumination lens, the objective lens and aperture having defined numerical apertures; light radiation 203 for the mask 1 on which a pattern relating to fabrication of semiconductor devices is formed; light detection 204 by the photodiode array 6; comparison process 205 between measurement data and reference data; detection 206 of wave dull in measurement data; and compensation 207 of wave dull. The detection 206 of wave dull and compensation 207 of wave dull are effected according to patterns to be inspected, as shown in FIG. 5.

As is shown in FIG. 5, there are at least two patterns to be inspected. Specifically, a mask 300, on one surface of which a phase member 301 is formed, is subjected to photoetching, thereby obtaining a pattern 303 having a phase member 302 with a substantially right-angled edge portion and a pattern 305 having a phase member 304 with a tapered edge portion.

In the above inspection apparatus, design data is subjected to a filtering process, in consideration of resolution characteristics of the objective lens 5 and aperture effect of the photodiode array 6. Thus, an estimated measurement signal profile of a pattern is calculated, as shown in FIG. 6.

In FIG. 6, the estimated measurement signal profile is obtained as a waveform defined by symbol D. Symbol D indicates the measurement signal, and symbol * indicates coincidence between the measurement signal S and estimated measurement signal D obtained by calculation. Each waveform as shown in FIG. 6 represents the result of observation on an area where a Cr pattern 21 is formed on a part of the mask 2, as shown in FIG. 7.

On the other hand, when an actual pattern is observed, a measurement signal waveform, as indicated by signal S, is obtained, as shown in FIG. 6.

As seen from FIG. 6, it is generally observed that a calculation value differs greatly from an actual measurement value in the vicinity of an edge portion of the pattern. If a calculation result is obtained so as to correct a wave dull near the pattern edge, the inclination of the entire pattern does not coincide. If the inclination of the entire pattern is corrected, the wave dull near the pattern edge is not corrected, as shown in FIG. 6. Although the causes of the wave dull of the actual measurement signal waveform near the pattern edge is not clearly understood, the following may be possible:

(1) The objective lens is not an ideal one, (2) A signal becomes dull due to a flare, etc. occurring within the optical system, and (3) The characteristics of the sensor at the start of operation are not good.

Since a large difference occurs between the calculation value and actual measurement value near the pattern edge, the conventional apparatus has a problem: the defect detection ratio is not enhanced when very small defects are present near the pattern edge.

Considering this fact, the inventors adopted the conventional method of emphasizing the vicinity of the pattern edge in the inspection apparatus. The actual measurement signal profile is approximated to the estimated signal profile obtained from the above calculation, thereby greatly enhancing the detection sensitivity as in the prior art.

The method for emphasizing the vicinity of the pattern edge will now be described. FIG. 8 shows a variation in a response function in the case where the ratio σ of the numerical aperture of the illumination lens of the illumination optical system to the numerical aperture of the objective lens is employed as a parameter. The abscissa S indicates the frequency of the pattern and the ordinate R indicates the response characteristics of the optical system.

In the conventional apparatus, the ratio σ of the numerical aperture is generally set at $\sigma \geq 1$. The reason for this is that it has conventionally been thought better to perform an inspection under the condition of $\sigma \geq 1$, in which case a response function extends to high frequencies. In addition, if the ratio σ is decreased excessively, an overshoot of a signal increases at the edge portion, as shown in FIG. 9 (indicating an image intensity distribution at the time of measuring the pattern edge portion). As a result, as seen from the above explanation of the comparison algorithm, the difference between the calculation value and the actual measurement value increases by a degree corresponding to the overshoot, resulting in erroneous detection of the presence of defects.

In many cases, however, a maximum frequency band of a defect which need be actually detected is near a frequency indicated by a broken line in FIG. 8. If the ratio σ is decreased to a certain degree, the response characteristics of the optical system in this band increases. Moreover, it is desired to lower the cut-off frequency in order to avoid unnecessary detection of defects over the maximum frequency of defects which are sought to be detected.

In the meantime, FIG. 8 is a knife edge image obtained experimentally by Charman (Handbook of Optical Techniques, Rev. Edit., Asakura-Shoten (1976). According to the experimental result, some overshoot already appears in the measured result with the ratio σ=0.8. From this result, only about 0.9 can be expected as ratio σ at which no overshoot occurs when a Cr pattern of the mask is observed. With the ratio σ of this degree, remarkable enhancement of the responsiveness of the optical system cannot be expected.

However, since the optical system of the inspection apparatus is complex, as mentioned above, the inventors paid attention to the fact that the wave dull of the actually measured signal waveform is large near the pattern edge, possibly due to causes (1) to (3). The inventors thought that no overshoot occurs in an actual measurement value even if ratio σ=0.8 or less and that there is a value of ratio σ which matches well with a result obtained by calculation. The inventors, therefore, thought that an inspection apparatus having higher detection sensitivity than in the prior art can be provided by adopting this value of ratio σ.

Figures 10, 11:
FIG. 10 illustrates improved optical properties obtained when a σ stop is inserted.
FIG. 11 shows improvement of defect detection when an inspection was performed with the ratio σ decreased to such a degree that no overshoot was observed in a measurement signal obtained at the pattern edge.

FIG. 10 shows the result of experiments relating to the above. FIG. 10, like FIG. 6, shows a measurement result and a calculation result near a pattern edge, which were obtained when the ratio σ=0.7. According to experiments with various values of ratio σ, it was found that such a great overshoot as is known in the prior art did not occur up to the ratio σ of about 0.65.

FIG. 11 shows actual evaluation results of defect detection performance in the case where ratio σ=0.7. As is shown in FIG. 11, the defect detection ratio near an edge (a hatched portion in a pattern shape indicates a Cr portion) was remarkably improved. It should be noted that FIG. 11 is a table showing defect detection ratios at edge and slanting edge portions, and an area below a thick solid line indicates that the defect detection ratio is 100%. In the result of the inspection with the prior-art profile shown in FIG. 6, a defect having a size of 0.25 μm was not 100%. However, when the ratio σ was set at 0.65, the defect with this size matched well with the result of the measurement profile obtained by calculation. Thus, the defect detection ratio reached 100% (indicated by hatching).

A problem in a practical aspect is that the light amount is only 49% when the ratio σ=0.7, as compared to the case where the ratio σ=1. As a result, the dynamic range of the gain of a sensor circuit needs to be increased to double or more. It is a feasible way to design the illumination optical system to set the light amount at an optimal level, with the ratio σ fixed at 0.7. However, the ratio σ of the inspection apparatus cannot be fixed at 0.7 because mask patterns of various materials, in addition to the Cr pattern, need to be inspected.

The sensor circuit of this type of inspection apparatus is optimally designed to reduce a noise level. Therefore, it is undesirable, from the standpoint of an inspection apparatus, to increase the dynamic range of the gain and to raise the noise level of the circuit. Even without such design modifications, the gain needs to be set to compensate for a decrease in light amount of the light source due to a time-basis variation, and the sensitivity and offset of each sensor pixel. It should be avoided, from an aspect of system design, to unnecessarily increase the dynamic range of the gain and to put an excessive load on the sensor circuit.

There is another method in which the light amount of the light source is varied and an increase in dynamic range of a circuit gain is prevented. This method, however, has a problem in that the automation is not easy and a long time is needed until the light amount of the light source is stabilized after the light amount is varied.

According to a method of the present invention, the light amount is controlled by light amount adjusting means such as a filter in accordance with a variation in ratio σ, thereby maintaining the amount of light input to the sensor at a substantially constant level and preventing an increase in dynamic range of the gain of the sensor circuit.

FIGS. 12A, 12B and 12C are cross-sectional views of a σ stop structure (aperture) 31. As is shown in FIGS. 12A, 12B and 12C, the σ stop mechanism is a kind of aperture, by which illumination light is shielded at a pupil position of the illumination system to vary the σ value. The $(r/r_1)$ ratio corresponds to the numerical aperture, wherein r is the radius of the aperture 31 and $r_1$ is the radius of the aperture 31 at the time when σ=1.

Figure 13A:
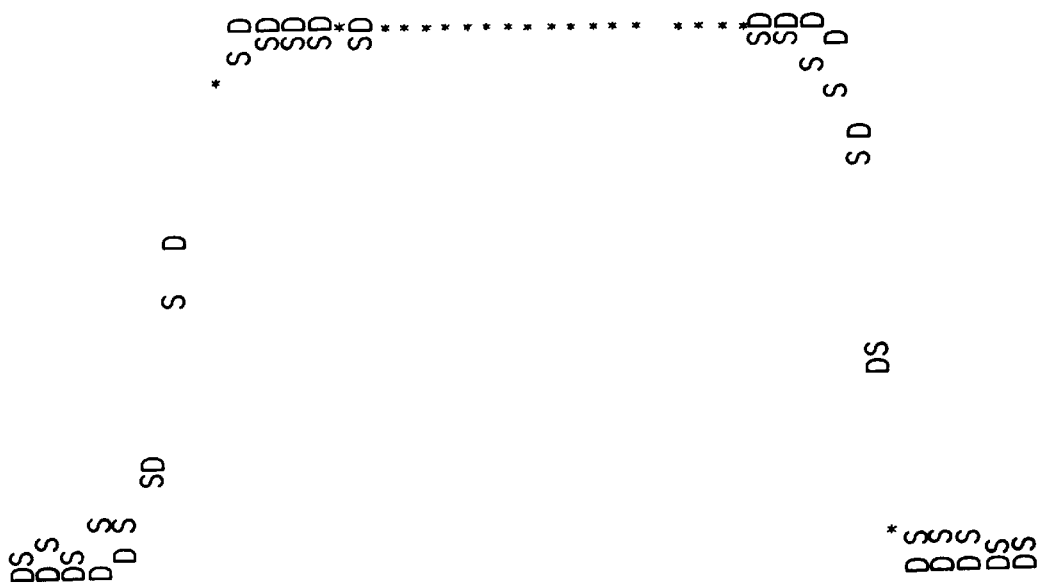
FIGS. 13A, 13B, 13C and 13D illustrate the relationship between the σ stop and the edge profile.
Figure 13B:
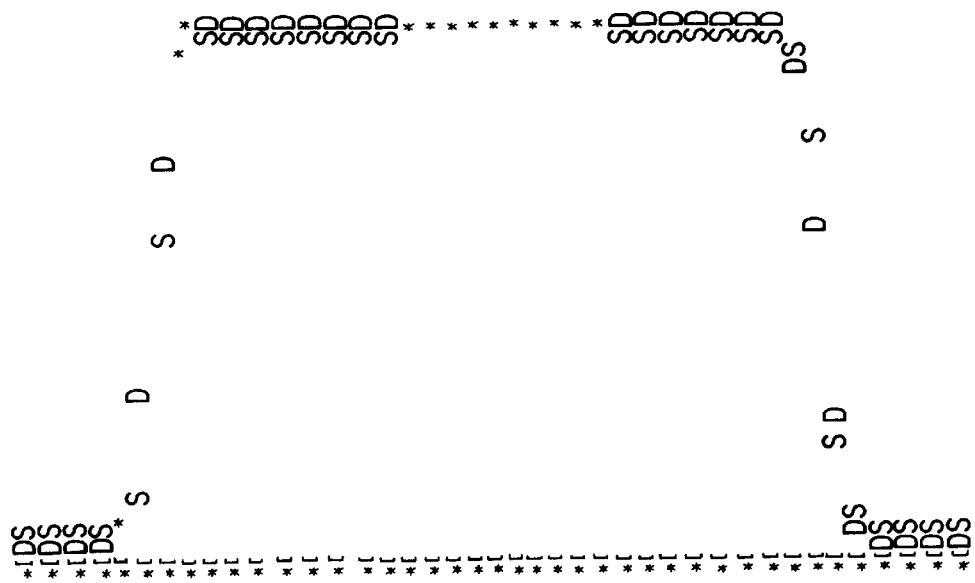

The relationship between the σ stop and the pattern edge profile will now be described with reference to FIGS. 13A to 13D. FIG. 13A shows an estimated measurement signal profile indicated by symbol D and a measurement signal indicated by symbol S in the case where σ=1. A wave dull occurs at an edge portion of the measurement data and thus the symbols S and D do not coincide. FIG. 13B shows an estimated measurement signal profile indicated by symbol D and a measurement signal indicated by symbol S in the case where σ=0.8. The symbols S and D coincide substantially.

Figure 13C:
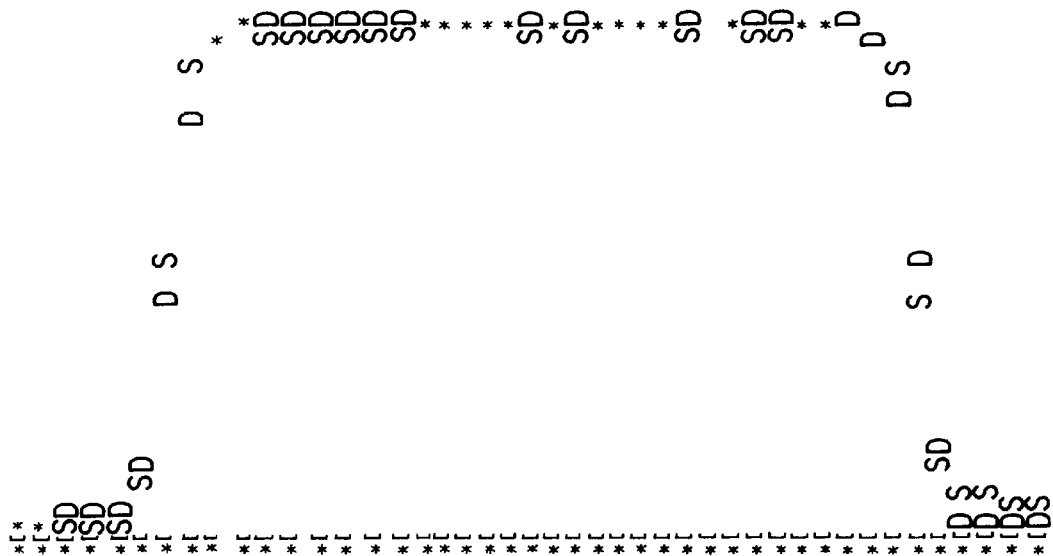
Figure 13D:
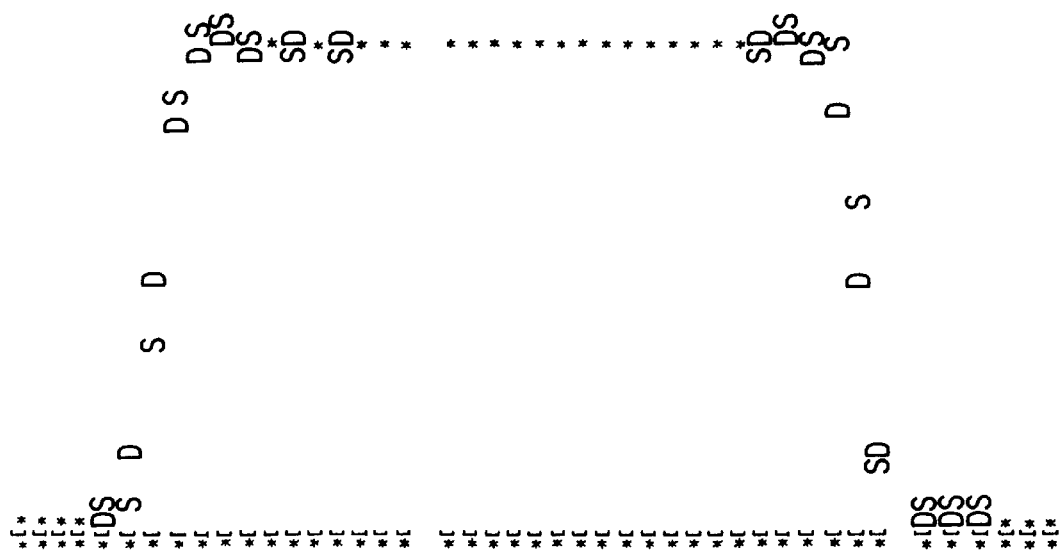

FIG. 13C shows an estimated measurement signal profile indicated by symbol D and a measurement signal indicated by symbol S in the case where σ=0.7. The symbols S and D coincide satisfactorily. FIG. 13D shows an estimated measurement signal profile indicated by symbol D and a measurement signal indicated by symbol S in the case where σ=0.6. A slight overshoot occurs in the measurement data and thus the symbols S and D coincide partially.

In the present invention, when the aperture has the ratio σ of a minimum value obtained by the experiments the filter is not provided (r=$r_0$), as shown in FIG. 12A. When the aperture has the ratio σ of a higher value, the filter 32 corresponding to the ratio $(r/r_1)^2$ (r=the radius of the aperture) is situated adjacent to the aperture having the ratio σ of a value greater than the minimum value. Thereby, the amount of light obtained with the aperture of the minimum ratio σ can be substantially maintained. The filter 32 is formed of, e.g., glass material. An optical filter 32a is formed on one or both sides of the filter 32. The aperture 31 and filter 32 may be fixed or individually inserted into the illumination optical system. In this case, the combination of the aperture 31 and filter 32 is predetermined and these are inserted and removed at the same time.

In the case where the σ stop mechanism 33 is constituted by the aperture 31 and filter 32, the σ stop mechanism 33 may be constituted as one unit, as shown in FIG. 12C, which comprises a glass plate 34, an aperture 35 formed by depositing a metal, etc. on the glass plate 34, and an optical filter 32a. In the σ stop mechanism 33 shown in FIG. 12C, a glass with no filter is provided even in the case where the ratio σ=1. Thus, even if various types of stop mechanisms 33 are inserted, there is no difference in optical path. Thus, the structure of FIG. 12C is better. By using the σ stop mechanism 33, the amount of light input to the sensor is made constant, the optimal circuit design can be made, and a stable inspection apparatus with a lowest noise level and high inspection performance can be realized.

Figure 15:
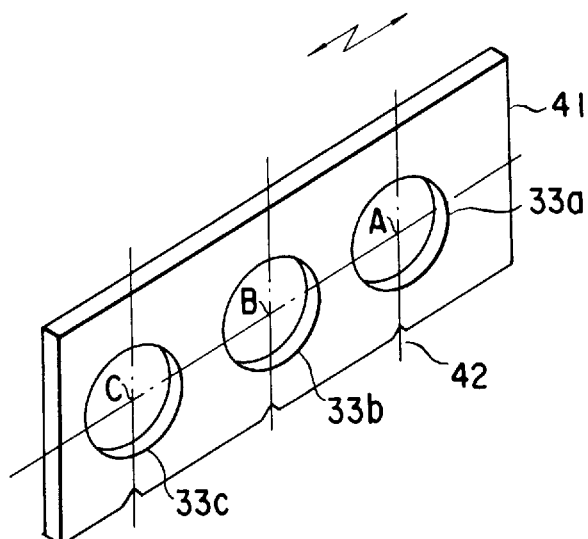
FIG. 15 shows an example of the σ stop mechanism according to the present embodiment.

As is shown in FIG. 14, the σ stop mechanism 33 is situated, for example, on the emission side of an integrator 38, which is opposed to the mask surface. The emission side corresponds to the pupil position of the illumination system within the illumination optical system. In order to vary the value σ, various apertures are prepared, as shown in FIG. 15. An aperture fixing jig 41 is moved by means of a motor, etc. on an as-needed basis, thereby aligning the center A, B or C of the σ stop mechanism 33a, 33b or 33c with the optical axis. The alignment is performed, for example, by engaging an alignment pin with notches 42, as shown in FIG. 15.

Figure 16:
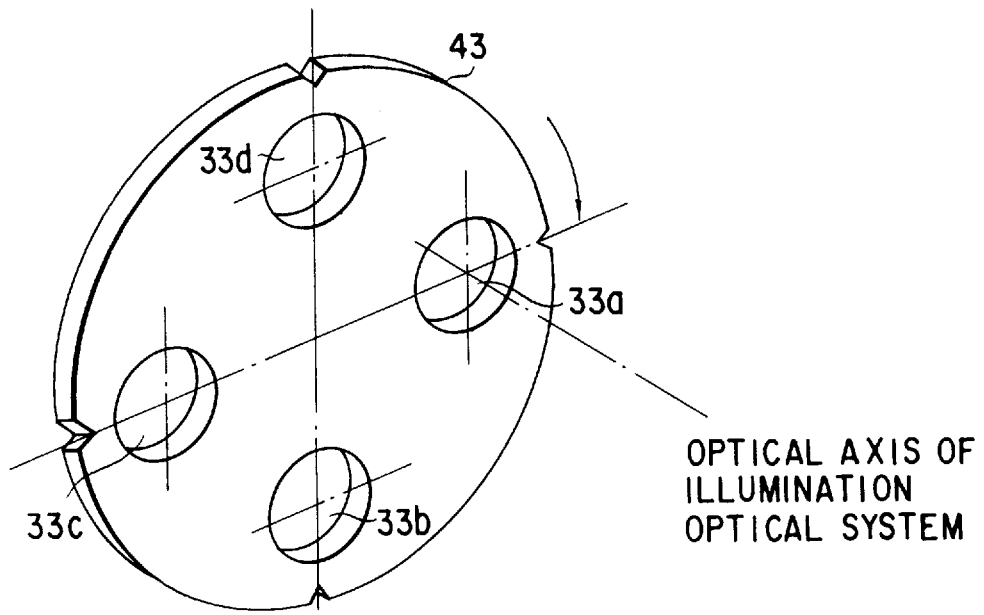
FIG. 16 shows another example of the σ stop mechanism according to the present embodiment.

Since the filter for making the amount of light constant is formed integral with the aperture, the amount of light incident on the sensor is automatically made constant. The aperture fixing jig 43 may have a plate-like shape, as mentioned above, or a circular shape, as shown in FIG. 16. In this case, the optical axis of the illumination optical system agrees with the center A of the σ stop mechanism 33a. The σ stop mechanism 33 is changed by the rotation of the aperture fixing jig 43. The σ stop mechanism 33 may be fixed to the aperture fixing jig 41 or 43 by means of a screw, etc. Thereby, the value σ and filter coefficient can be finely adjusted in accordance with the characteristics of individual inspection apparatuses.

The driving system may be designed to be controlled by a computer. The driving system may be designed to be automatically changed according to the type of a pattern (e.g., a Cr pattern, a phase-shift pattern, an X-mask pattern, etc.) to be inspected, which is designated by the operator. The above-described structures are very simple and practical. It is possible, as mentioned above, that the aperture and filter are manufactured separately so that they may be changed independently, and that the aperture and filter are driven synchronously so that the amount of light incident on the sensor may be made constant.

Figure 2:
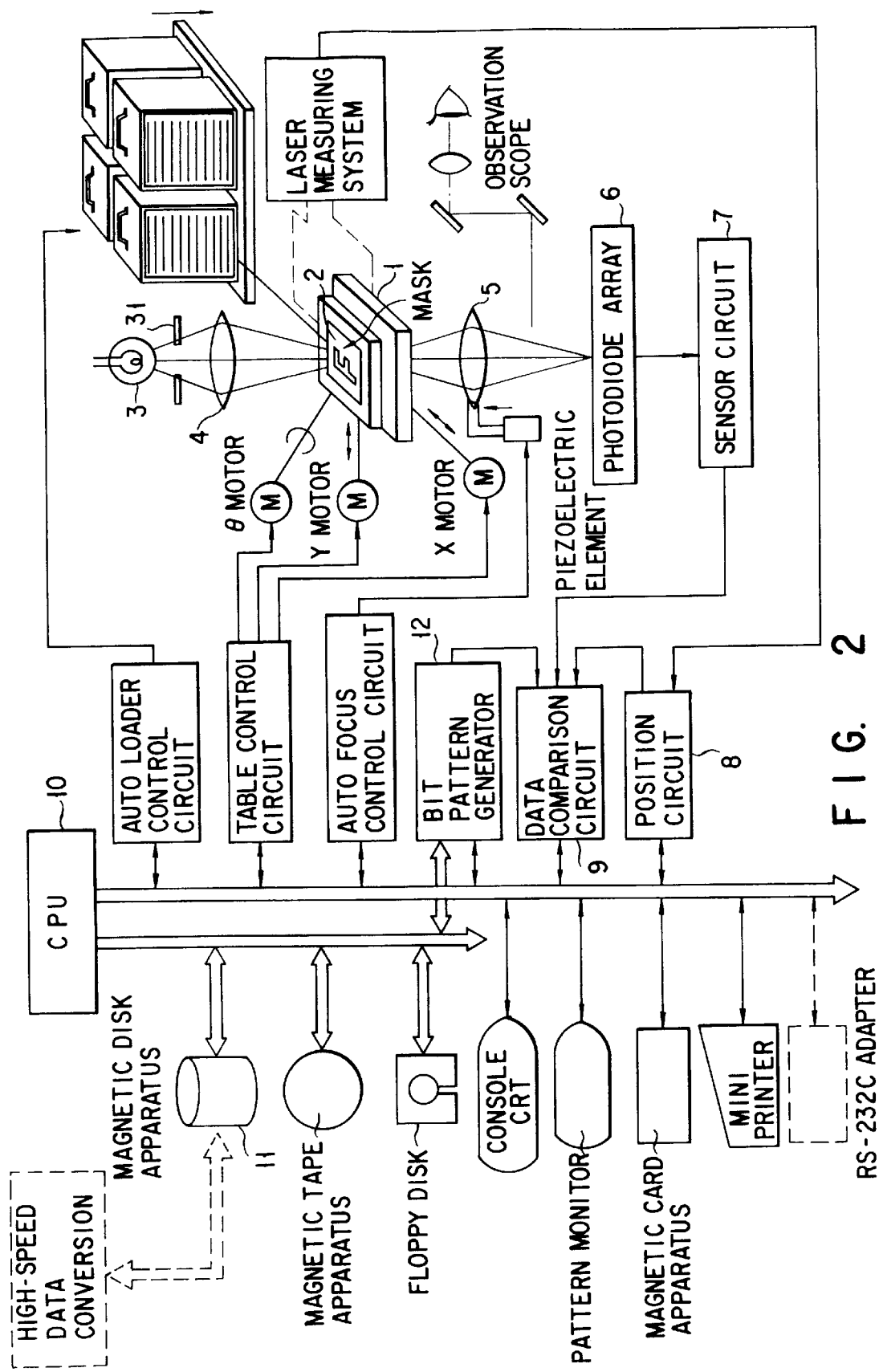
FIG. 2 shows a system structure of a sample inspection apparatus.

This type of inspection apparatus may be used with the projection magnification of a pattern on the photodiode array 6 shown in FIG. 2 being varied. In this case, too, the aperture and filter of the σ stop mechanism 33 can be changed on an as-needed basis, without departing from the subject matter of the invention.

According to the present embodiment, attention is paid to the fact that a wave dull of an actually measured waveform due to the above-mentioned causes (1) to (3) is large near a pattern edge. It is commonly known that an overshoot appears in an actual measurement value near an edge portion when the ratio σ is normally about 0.8. It was confirmed, however, that no overshoot occurs up to the ratio σ of 0.65, and the ratio σ in numerical aperture (NA) between the illumination lens of the illumination optical system and the objective lens was changed to the above value. Thereby, the degree of coincidence between the edge profile obtained by calculation and the actual measurement profile, which is the most important parameter in an inspection apparatus, was enhanced.

In addition, the σ stop aperture and filter are combined to make constant the amount of light incident on the sensor. Thereby, the sensor circuit can be optimally designed to decrease the noise level. As a result, the inspection apparatus with a minimum noise level can be obtained. With the inspection apparatus thus constructed, the defect detection ratio near the edge can remarkably be enhanced as compared with the prior art.

Furthermore, the present apparatus can be used with a relatively low σ value. Accordingly, enhancement in MTF can be expected, the signal intensity of the defective portion can be improved, and the cut-off frequency can be decreased. It is possible, therefore, to detect high-frequency defects unnecessarily. Furthermore, a proper σ value can be chosen in accordance with various objects to be inspected, and a practical defect inspection apparatus with a high S/N can be provided.

The present invention is not limited to the above embodiments. In the embodiments, design data is used as data to be compared with measurement data. However, a second unit of measurement data corresponding to the same pattern image as a first set of measurement data may be used. Specifically, two chips on which the same pattern is formed can be observed by different detection means and compared with each other. The light amount adjusting means is not limited to the means for adjusting the light transmissivity at the aperture for varying the ratio of the numerical aperture (NA), but may be any means which is provided between the light source and light receiving element and can vary the light transmissivity.

As has been described above in detail, according to the sample detection apparatus of the present invention, the ratio of the NA of the illumination lens to the NA of the objective lens is varied in accordance with the kind of the pattern to be tested. In addition, the variation in amount of light received by the light receiving element due to the variation of the ratio of the NA is reduced. Thereby, a defect of a size less than the minimum size detected by the conventional apparatus can be detected. Moreover, a defect, in particular, near an edge portion of a pattern can be detected with high sensitivity.

FIG. 17 shows the relationship between the size of an edge defect and the detection ratio in the case where the ratio σ is 1 or 0.7. FIG. 18 shows the relationship between the size of an isolated defect and the detection ratio in the case where the ratio σ is 1, 0.9, 0.8 or 0.7. As is obvious from FIGS. 17 and 18, the performance of detection of not only the edge defect but also the isolated defect can be enhanced.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A sample inspection apparatus comprising:
    a light source radiating light on a sample on which a pattern relating to fabrication of a semiconductor device is formed;
    an illumination lens provided between said light source and said sample for illuminating light on said sample;
    light receiving means for detecting a light transmission image of the pattern on the sample on which the light has been radiated by said light source;
    an objective lens, provided between said sample and said light receiving means, focusing an image of the pattern on the sample onto said light receiving means;
    determination means for determining a presence/absence of a defect of the pattern by comparing measurement data corresponding to the light transmission image of the pattern obtained by said light receiving means with reference data relating to said pattern; and
    control means for controlling a ratio σ of a numerical aperture of said illumination lens to a numerical aperture of said objective lens, in accordance with a type of said pattern.

2. The sample inspection apparatus according to claim 1, wherein the reference data in said determination means is design data of said pattern.

3. The sample inspection apparatus according to claim 1, wherein the reference data in said determination means is measurement data of a pattern different from the pattern to be inspected.

4. The sample inspection apparatus according to claim 1, wherein the type of the pattern in said control means is determined by the type of shape of an edge portion of the pattern.

5. The sample inspection apparatus according to claim 1, wherein the ratio σ of the numerical aperture of said illumination lens to the numerical aperture of said objective lens in said control means is controlled by an optical element including an optical filter and an aperture.

6. The sample inspection apparatus according to claim 5, wherein said optical filter and said aperture in said optical element are constituted as one body.

7. The sample inspection apparatus according to claim 1, wherein the ratio σ of the numerical aperture of said illumination lens to the numerical aperture of said objective lens in said control means is controlled by a plurality of optical elements including an optical filter and an aperture and having different optical characteristics, and a mechanism for selecting one of said optical elements.

8. The sample inspection apparatus according to claim 7, wherein said mechanism includes a jig for removably fixing said plurality of optical elements.

9. The sample inspection apparatus according to claim 7, wherein said mechanism includes means for selecting one of said plurality of optical elements based on the type of the pattern.

10. A sample inspection apparatus comprising:
    a light source radiating light on a sample on which a pattern relating to fabrication of a semiconductor device is formed;
    an illumination lens provided between said light source and said sample for illuminating light on said sample;
    light receiving means for detecting a light transmission image of the pattern on the sample on which the light has been radiated by said light source;
    an objective lens, provided between said sample and said light receiving means, focusing an image of the pattern on the sample onto said light receiving means;
    determination means for determining a presence/absence of a defect of the pattern by comparing measurement data corresponding to the light transmission image of the pattern obtained by said light receiving means with reference data relating to said pattern; and
    control means for controlling said light source such that a ratio σ of a numerical aperture of said illumination lens to a numerical aperture of said objective lens is varied and an output of said light receiving means is substantially constant when the ratio σ of the numerical aperture is varied.

11. The sample inspection apparatus according to claim 10, wherein said control means is operated in accordance with a type of the pattern to be inspected.

12. The sample inspection apparatus according to claim 11, wherein the type of the pattern in said control means is determined by the type of shape of an edge portion of the pattern.

13. The sample inspection apparatus according to claim 10, wherein the reference data in said determination means is design data of said pattern.

14. The sample inspection apparatus according to claim 10, wherein the reference data in said determination means is measurement data of a pattern different from the pattern to be inspected.

15. The sample inspection apparatus according to claim 11, wherein said control means includes an aperture for varying the ratio σ of the numerical aperture of said illumination lens to the numerical aperture of said objective lens.

16. The sample inspection apparatus according to claim 11, wherein said control means includes means for varying light transmissivity.

17. The sample inspection apparatus according to claim 11, wherein said control means includes an optical filter for making an output of said light receiving means substantially constant when the ratio σ of the numerical aperture is varied.

18. The sample inspection apparatus according to claim 11, wherein said control means includes an aperture for varying the ratio σ of the numerical aperture of said illumination lens to the numerical aperture of said objective lens, and an optical filter for making an output of said light receiving means substantially constant when the ratio σ of the numerical aperture is varied.

19. The sample inspection apparatus according to claim 18, wherein said aperture and said optical filter are constituted as one body.

20. The sample inspection apparatus according to claim 11, wherein said control means includes a plurality of optical elements including an optical filter and an aperture and having different optical characteristics, and a mechanism for selecting one of said optical elements.

21. The sample inspection apparatus according to claim 20, wherein said mechanism includes a jig for removably fixing said plurality of optical elements.

22. The sample inspection apparatus according to claim 21, wherein said mechanism includes means for selecting one of said plurality of optical elements based on the type of the pattern to be inspected.

23. A sample inspection method comprising the steps of:
radiating light on a sample, on which a pattern relating to fabrication of a semiconductor device is form via an illumination lens;
receiving the light for detecting a light transmission image of the pattern on the sample via an objective lens on which the light has been radiated in said light radiation step;
focusing an image of the pattern on said sample;
determining the presence/absence of a defect of the pattern by comparing measurement data corresponding to the light transmission image of the pattern obtained in said light receiving step with reference data relating to said pattern; and
controlling the ratio $\sigma$ of the numerical aperture of said illumination lens to the numerical aperture of said objective lens, in accordance with type of said pattern.

24. The sample inspection method according to claim 23, wherein said ratio $\sigma$ is $1<\sigma\leq 0.65$.

25. A sample inspection method comprising the steps of:
radiating light on a sample, on which a pattern relating to fabrication of a semiconductor device is formed via an illumination lens;
receiving the light for detecting a light transmission image of the pattern on the sample via an objective lens on which the light has been radiated in said light radiation step;
focusing an image of the pattern on said sample;
determining a presence/absence of a defect of the pattern by comparing measurement data corresponding to the light transmission image of the pattern obtained in said light receiving step with reference data relating to said pattern; and
controlling said light radiation step, thereby executing an operation of varying a ratio $\sigma$ of a numerical aperture of said illumination lens to a numerical aperture of said objective lens, and an operation of making an output in said light receiving step substantially constant even when the ratio $\sigma$ of the numerical aperture is varied.

26. The sample inspection method according to claim 25, wherein said ratio $\sigma$ is $1<\sigma\leq 0.65$.

27. A sample inspection method wherein light is radiated on a sample on which a pattern relating to fabrication of a semiconductor device is formed, via an optical system having an illumination lens and an objective lens both having specified numerical apertures, thereby detecting a light transmission image of said pattern by light receiving means, and a presence/absence of a defect of the pattern is determined by comparing measurement data corresponding to the light transmission image of the pattern obtained by said light receiving means with reference data relating to said pattern, said method comprising the steps of:
detecting a signal wave dull in said measurement data at an edge portion of the pattern; and
compensating the wave dull detected in said detecting step by controlling a ratio $\sigma$ of the numerical aperture said illumination lens to the numerical aperture of said objective lens.

28. The sample inspection method according to claim 27, wherein said ratio $\sigma$ is $1<\sigma\leq 0.65$.

* * * * *